(12) United States Patent
Kim

(10) Patent No.: US 9,005,232 B2
(45) Date of Patent: Apr. 14, 2015

(54) LANCET SYSTEM

(71) Applicant: Stanley I. Kim, Upland, CA (US)

(72) Inventor: Stanley I. Kim, Upland, CA (US)

(*) Notice: Subject to any disclaimer, the term of this patent is extended or adjusted under 35 U.S.C. 154(b) by 0 days.

(21) Appl. No.: 14/171,473

(22) Filed: Feb. 3, 2014

(65) Prior Publication Data

US 2014/0228873 A1 Aug. 14, 2014

Related U.S. Application Data

(63) Continuation of application No. 12/452,314, filed as application No. PCT/US2008/070666 on Dec. 26, 2009, now Pat. No. 8,647,356.

(60) Provisional application No. 61/128,142, filed on May 19, 2008, provisional application No. 61/125,096, filed on Apr. 22, 2008, provisional application No. 61/124,281, filed on Apr. 16, 2008, provisional application No. 61/123,009, filed on Apr. 4, 2008, provisional application No. 61/030,975, filed on Feb. 24, 2008, provisional application No. 61/062,696, filed on Jan. 29, 2008, provisional application No. 61/010,459, filed on Jan. 9, 2008.

(51) Int. Cl.
*A61B 17/14* (2006.01)
*A61B 5/15* (2006.01)
*A61B 5/151* (2006.01)

(52) U.S. Cl.
CPC ..... *A61B 5/150969* (2013.01); *A61B 5/150396* (2013.01); *A61B 5/150427* (2013.01); *A61B 5/1411* (2013.01); *A61B 5/15142* (2013.01)

(58) Field of Classification Search
CPC ............ A61B 5/150969; A61B 5/150396; A61B 5/15142; A61B 5/1411; A61B 17/32053; A61B 5/14532; A61B 5/15186; A61B 5/15146; A61B 5/150022; A61B 5/150412; A61B 5/151; A61B 17/32093; A61B 5/15105; A61B 5/150389; A61B 5/150427
USPC .......... 606/181, 182, 183; 604/136, 137, 138, 604/139; 600/583
See application file for complete search history.

(56) References Cited

U.S. PATENT DOCUMENTS

| | | | | |
|---|---|---|---|---|
| 5,395,387 A | * | 3/1995 | Burns | 606/181 |
| 5,741,288 A | * | 4/1998 | Rife | 606/181 |
| 8,647,356 B2 | * | 2/2014 | Kim | 606/181 |
| 2005/0234487 A1 | * | 10/2005 | Shi | 606/181 |

OTHER PUBLICATIONS

Tempo: Perfecting the Art of the Needle as accessed Jul. 16, 2014; http://www.tempobalance.com/?page_id=16.*

* cited by examiner

*Primary Examiner* — Jonathan W Miles
(74) *Attorney, Agent, or Firm* — Michael Fredrick; Loza & Loza, LLP

(57) ABSTRACT

A lancing system comprising a lancet with a handle portion and a needle bearing portion, the needle bearing portion retaining a thin needle protected by a safety cap. The safety cap includes first and second chambers, where the first chamber acts as a sheath and the second chamber having a surface positioned to compromise the structure of the needle when the needle bearing portion of the lancet body is inserted into the second chamber.

16 Claims, 11 Drawing Sheets

Fig. 5A
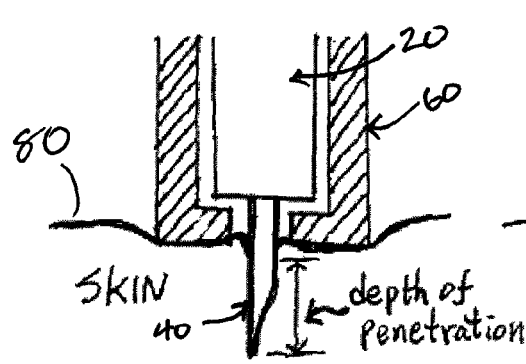
Fig. 5B
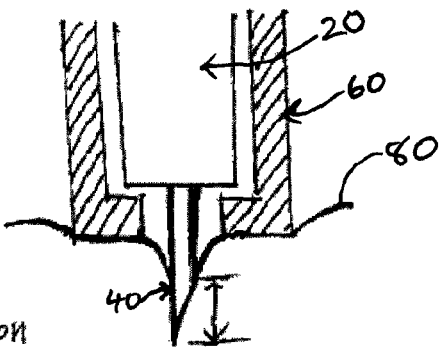
Fig. 5C
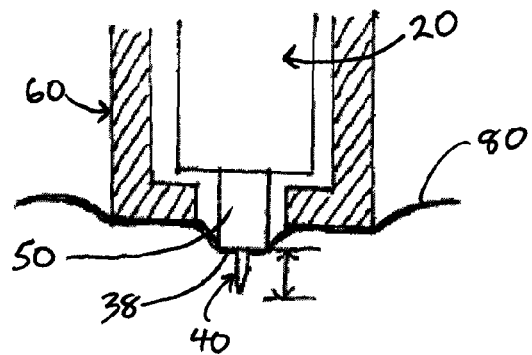
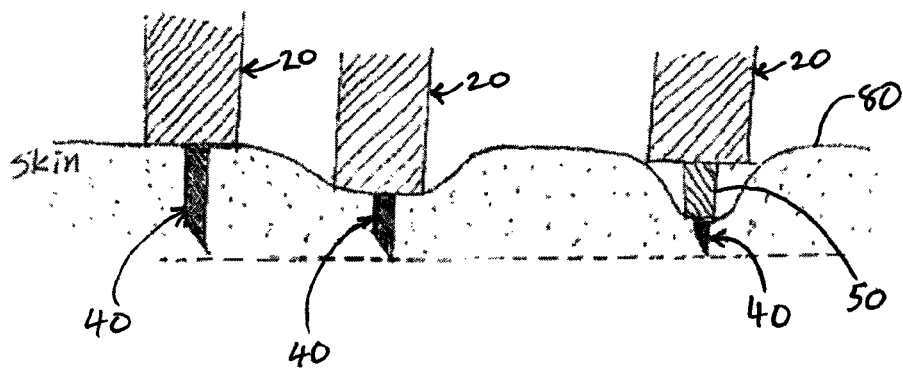
Fig. 5D

Fig. 6E   Fig. 6F
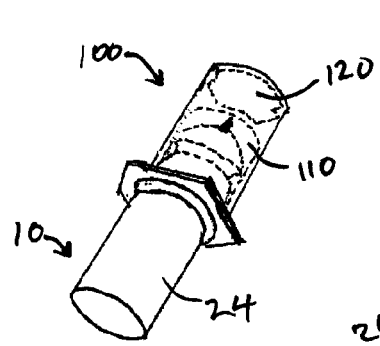 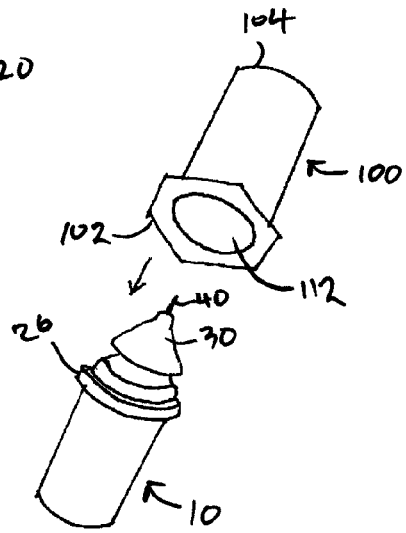
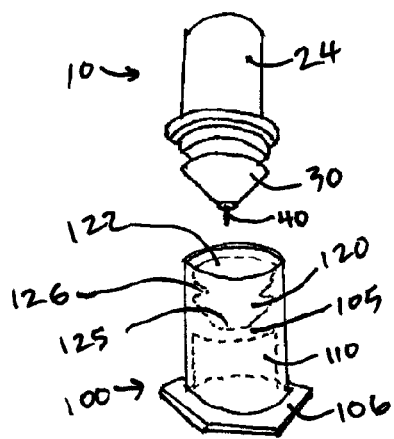 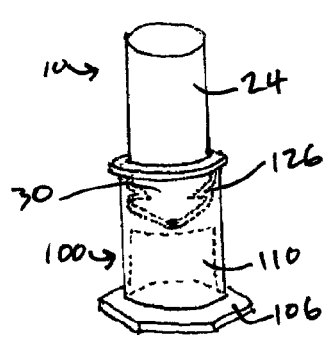
Fig. 6G   Fig. 6H

Fig. 7A   Fig. 7B   Fig. 7C
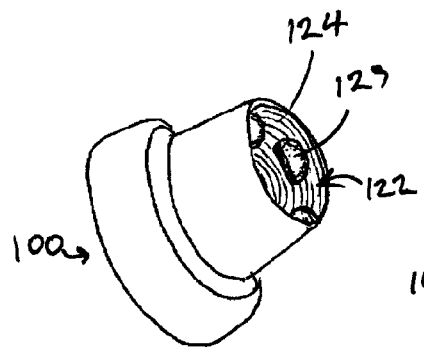
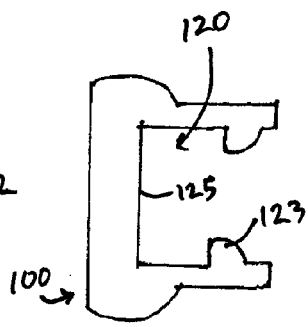
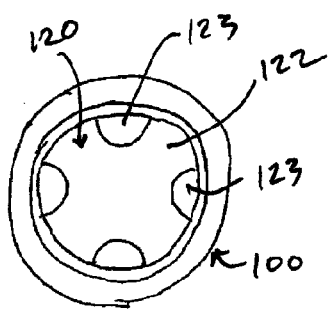
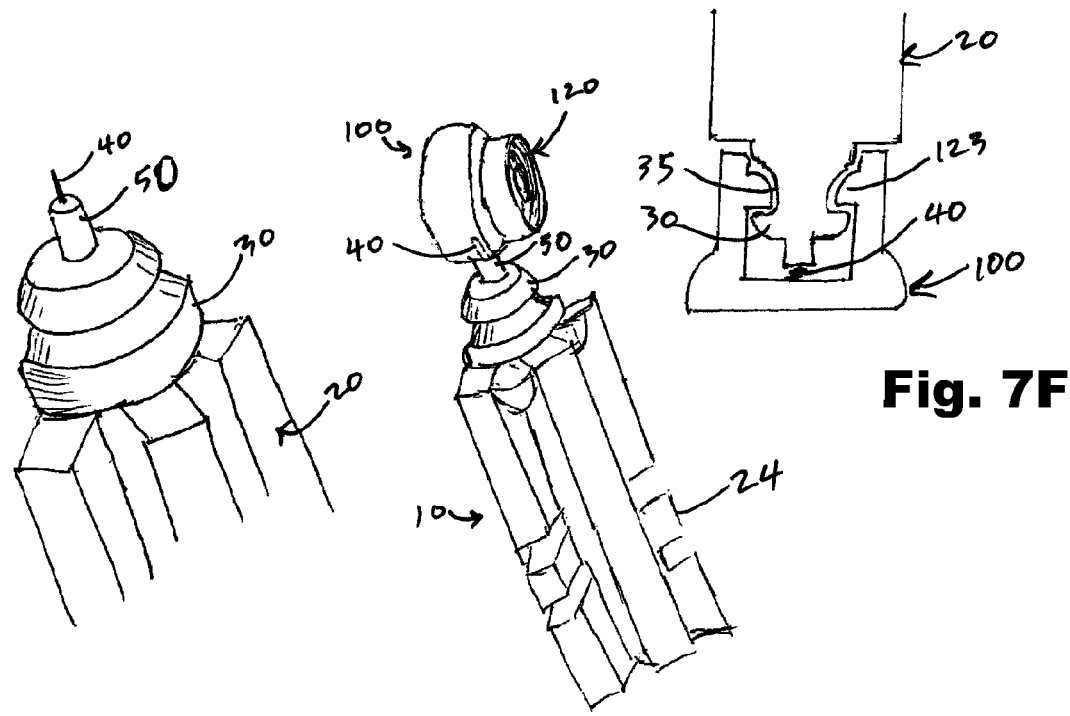
Fig. 7D
Fig. 7E
Fig. 7F

Fig. 8C
Fig. 8D
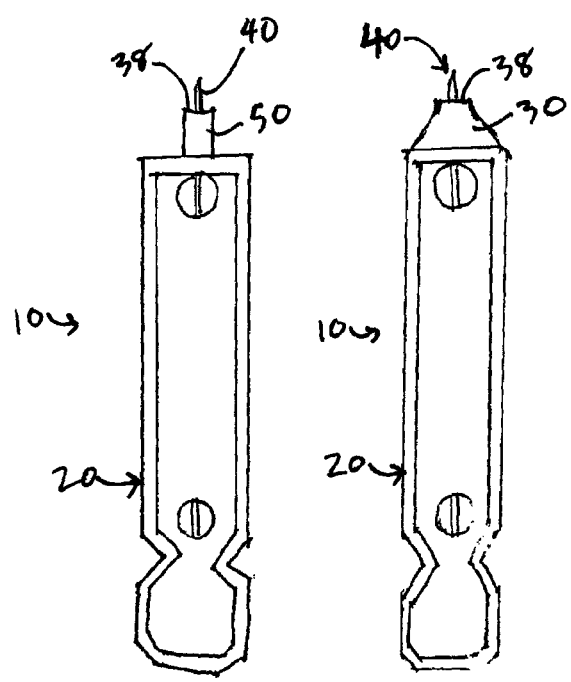
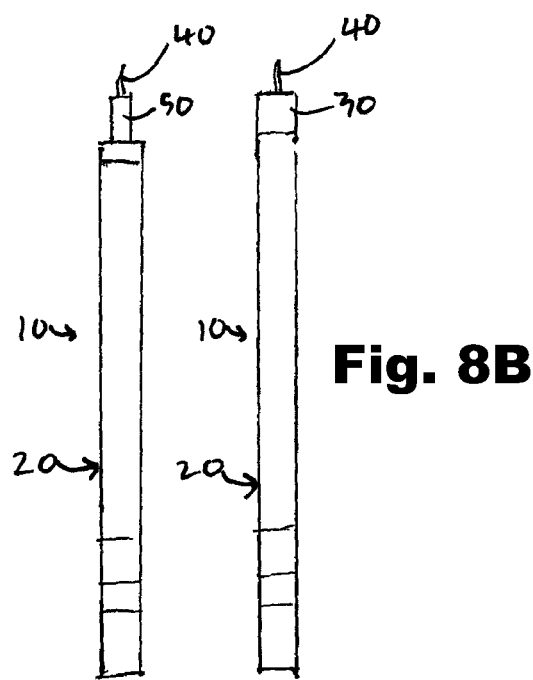
Fig. 8B
Fig. 8A

LANCET SYSTEM

CROSS-REFERENCE TO RELATED APPLICATIONS

The present application claims priority from the following prior U.S. patent applications: U.S. Provisional Patent Application No. 60/961,411, filed Jul. 21, 2007, entitled "A lancet with a very thin and short needle and a safety cap;" U.S. Provisional Patent Application No. 61/007,876, filed Dec. 15, 2007, entitled "Lancet with a very thin and short needle suitable for a child;" U.S. Provisional Patent Application No. 61/010,459, filed Jan. 9, 2008, entitled "A safety locking system for a used blood lancet;" U.S. Provisional Patent Application No. 61/062,696, filed Jan. 29, 2008, entitled "Lancet cap for a lancet with very thin and short needle;" U.S. Provisional Patent Application No. 61/030,975, filed Feb. 24, 2008, entitled "A lancet cap having flanges;" U.S. Provisional Patent Application No. 61/123,099, filed Apr. 4, 2008, entitled "Lancet needle reinforcement bar;" U.S. Provisional Patent Application No. 61/124,281, filed Apr. 16, 2008, entitled "Flat lancet with a thin and short needle," U.S. Provisional Patent Application No. 61/125,096, filed Apr. 22, 2008, entitled "A flat lancet;" U.S. Provisional Patent Application No. 61/128,142, filed May 19, 2008, entitled "Flat lancet with a pedestal;" and U.S. patent application Ser. No. 12/452,314, filed Dec. 26, 2009, entitled "Lancet System." The entire disclosure of each of the foregoing applications is hereby incorporated herein by reference.

BACKGROUND

Blood is subjected to various tests in connection with medical analyses. A widely practiced test used to monitor and treat diabetes is the determination of glucose levels in blood. Diabetic patients test their blood glucose levels on a frequent basis in order to monitor such levels.

To obtain blood for a glucose test, patients typically use a lancet having a needle which punctures the skin and thereby draws blood for the test. Typically, lancets are used in conjunction with a lancing device which propels a lancet toward the skin of a patient using a spring system. When the lancing device launches the lancet, the needle of the lancet is pushed forward through an exit hole located at the end of the lancing device and into the skin of the patient. The material forming the exit hole typically has a thickness of at least 1 mm, and lancet needles typically have a length of about 3 mm in order to be able to pass through the exit hole and puncture the skin of the patient. In view of this needle length, current lancet needles are generally in the range of 21-33 gauge. The substantial thickness and length of current lancet needles can be intimidating to users, and particularly to children.

When puncturing the skin of patient, a lancet can inflict pain. The amount of pain from a lancet puncture generally correlates with the size of the wound inflicted by the lancet, as well as with the location of the wound. Small lancet wounds may not provide enough blood for a sample, while large wounds may produce considerable pain and heal slowly.

Current lancets are typically provided with a cap having a single compartment that fits onto the lancet in order to cover the needle of the lancet both prior to and following use. However, a patient cannot tell whether a covered needle has been used without removing the cap and viewing the needle. A visual inspection of the needle may not be conclusive, and may lead a patient in some cases to reuse a non-sterile needle.

SUMMARY

Accordingly, there is a need for improved lancets and lancing systems that remedy the shortcomings of current lancing devices. The present lancets and lancing systems address this need, as they inflict less pain, are less intimidating, and can prevent accidental injury. In one embodiment, the present lancet has a body with a handle portion and a needle bearing portion comprising one or more needles. Preferably, the needle bearing portion of the lancet body has an upper surface with a first diameter at a distal end of the lancet body and a second surface proximal to the upper surface of the needle bearing portion with a second diameter. The first diameter is smaller than the second diameter, with the upper surface of the needle bearing portion in one embodiment tapering outwardly toward the second surface of the lancet. The needles in all embodiments are preferably at least 34 gauge.

The present lancets are preferably used together with a lancing device capable of retaining a lancet and urging it forward to puncture a skin surface of a user when actuated, the lancing device having an opening sized to allow the lancet needle(s) and at least the upper surface of the needle bearing portion of the lancet to pass through the opening. In this way, shorter and thinner needles than those used in present blood lancets can be used in the present lancets, and more consistent penetration of the skin surface can be achieved. Skin surfaces are preferably penetrated at a depth of from 0.5-1.0 mm in order to produce sufficient blood for testing but limit pain to patients. Preferably, the lancing device includes a depth adjustment mechanism.

The present lancing system can further comprise a safety cap having first and second compartments for receiving the needle(s) of the lancet, the first compartment being sized to accommodate the needle(s) of the lancet when they are inserted into the first compartment of the cap and the cap is removably secured to the lancet. The second compartment includes a surface positioned so as to contact the needle(s) of the lancet and compromise the structure of such needles when the lancet is inserted into the second end of the cap. In embodiments in which the safety cap is injection molded together with the lancet body, the first compartment can be formed around the needle or needles of the lancet at the same time that the lancet body is formed. In such embodiments, the weight of the lancet cap may be unevenly distributed, and in such cases a reinforcement bar attached to the safety cap and/or to the lancet body can be formed in order to stabilize the safety cap around the needle(s) of the lancet and prevent inadvertent bending of a needle while it is contained in the first compartment of the safety cap.

In one embodiment, the first and second compartments can be located at opposed ends of the safety cap, and the surface of the second compartment can be part of a divider between the first compartment and the second compartment. Optionally, the second compartment of the cap can be removably securable to the lancet. For example, the lancet body can be provided with threads that can be engaged with grooves in the first compartment of the cap. The cap can also have an indicator to distinguish the second end from the first end of the cap, so that lancet needles are not inadvertently compromised. In addition, the first end of the cap can have a flange or other support to allow the cap to be stood on the first end.

In another embodiment, the lancet body and the second compartment of the cap are designed to be fixedly secured to prevent needle stick injuries once the lancet is inserted into the second compartment of the cap. For example, the distal portion of the lancet body can comprise a protruding, preferably conical section which extends beyond the circumference of a more proximal portion of the lancet body, and the inner wall of the second compartment of the safety cap can comprise a circular recess for retaining a protruding section of the lancet body. Alternatively, the inner wall of the second compartment can comprise inwardly extending flanges for engaging the protruding section of the lancet body and preventing the withdrawal of the lancet from the safety cap.

DRAWINGS

FIG. 5A is a sectional view illustrating the penetration of a user's skin by a prior art lancet.

FIG. 5B is another sectional view illustrating the penetration of a user's skin by a prior art lancet.

FIG. 5C is a sectional view illustrating the penetration of a user's skin by an embodiment of the present lancet.

FIG. 5D is a sectional view illustrating the penetration of a user's skin by an embodiment of the present lancet as compared to prior art lancets.

FIGS. 6E-6H are perspective views illustrating the use of the lancet of FIG. 6A with the safety cap of FIG. 6C.

FIG. 7A is a perspective view of a safety cap of the present invention.

FIG. 7B is a sectional view of the safety cap of FIG. 7A.

FIG. 7C is a plan view of the safety cap of FIG. 7A showing the second chamber of the safety cap.

FIG. 7D is a perspective view of the distal end of an embodiment of a lancet of the present invention.

FIG. 7E is a perspective view of the safety cap of FIG. 7A retained on the lancet of FIG. 7D.

FIG. 7F is a sectional view showing the lancet of FIG. 7D after it has been inserted into the second chamber of the safety cap of FIG. 7A.

FIG. 8A is a plan view of an embodiment of the present lancet.

FIG. 8B is a side view of the lancet of FIG. 8A.

FIG. 8C is a plan view of another embodiment of the present lancet.

FIG. 8D is a side view of the lancet of FIG. 8C.

DETAILED DESCRIPTION

Definitions

Figure 1:
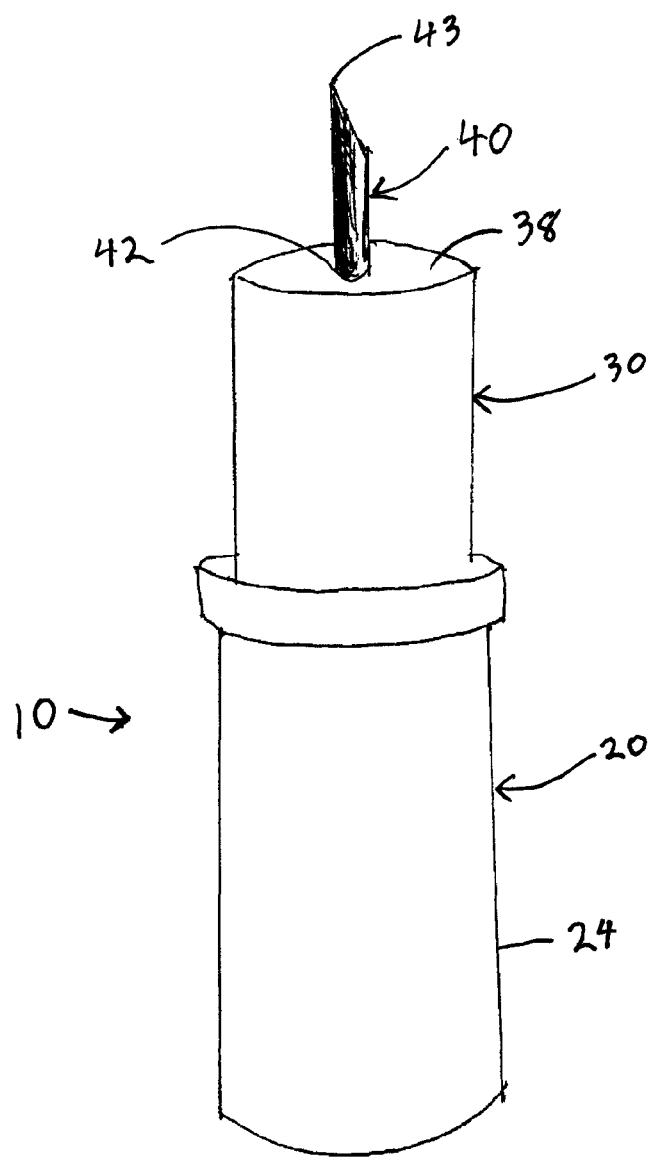
FIG. 1 is a perspective view of a prior art lancet.

As used herein, the following terms and variations thereof have the meanings given below, unless a different meaning is clearly intended by the context in which such term is used.

"About" means within 20% of a recited parameter or measurement, and preferably within 10% of such parameter or measurement.

"Chamber" means an enclosed or partially enclosed space. The present safety caps include one or more chambers, each of which includes an opening for receiving needle(s) and/or the needle bearing portion of the present lancet.

"Inwardly" means toward an interior portion of a device or component, or in a direction toward a longitudinal axis, depending on the context.

"Lancet" means a device comprising one or more needles capable of puncturing a skin surface of an individual in order to obtain a sample of blood.

"Lancing device" means a device which retains a lancet and which is capable of projecting one or more needles of the lancet through a skin surface of an individual.

The abbreviation "mm" indicates millimeters.

"Needle" means a sharp pointed implement.

"Outwardly" means in a direction away from a surface. If the surface is in an interior portion of a device or component, outwardly means toward an exterior portion of the device or component, or toward a point away from a longitudinal axis, depending on the context.

As used herein, the term "comprise" and variations of the term, such as

"comprising" and "comprises," are not intended to exclude other additives, components, integers or steps.

The terms "a," "an," and "the" and similar referents used herein are to be construed to cover both the singular and the plural unless their usage in context indicates otherwise.

Lancets

The present invention, according to a first embodiment, is directed to an improved lancet 10 for obtaining blood samples. As shown for example in FIG. 2, the present lancet 10 includes a body 20 which comprises a handle portion 24 and a needle bearing portion 30 for retaining one or more needles 40. The handle portion 24 can be configured to allow a patient to hold and manipulate the lancet, and preferably is also configured to be retained by a lancing device 60.

Needle Bearing Portion

Figure 4A:
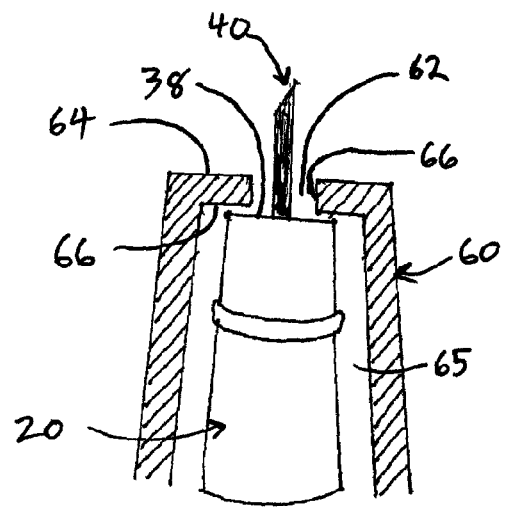
FIG. 4A is a sectional view of the distal portion of the prior art lancet of FIG. 1 within a lancing device.

As shown in FIG. 1, prior art lancets 10 typically have a single needle 40 extending from a distal surface 38 of the needle bearing portion 30. FIG. 4A further illustrates that when present lancets are used in current lancing devices 60, the distal surface 38 of the needle bearing portion 30 contacts an interior surface 66 of the lumen 65 of the lancing device 60, thereby stopping the outward progression of the lancet body 20 and preventing the lancet body 20 from passing through the exit opening 62 of the lancing device 60 and past the outer distal surface 64 of the lancing device 60. Because of this, only the needle 40 of the lancet 10 comes into contact with the skin of a user. Moreover, the needle 40 must be sufficiently long to be able to pass through all or part of the exit opening 62. This added length impacts the diameter of the needle 40, as longer needles must have a greater diameter in order to be strong enough to puncture the skin of a user without breaking.

Figure 4B:
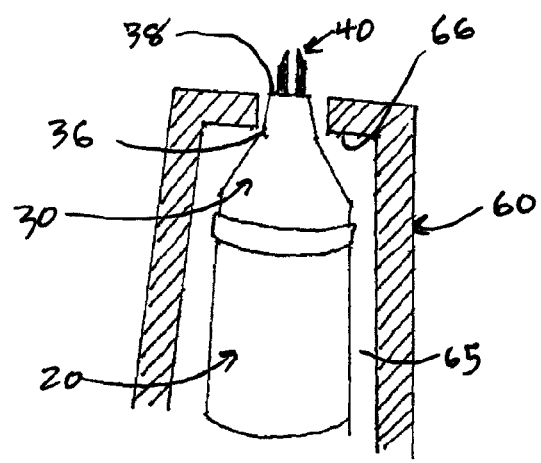
FIG. 4B is a sectional view of an embodiment of the present lancet within a lancing device.

The needle bearing portion 30 of the present lancet 10 differs from that of prior lancets in having a distal surface 38 which is sized and configured so as to be able to pass completely through the exit opening 62 of a lancing device 60, i.e. so that the distal surface 38 extends axially outward at least as far as the outer distal surface 64 of the lancing device 60, in which case the distal surface 38 would be approximately flush with the outer distal surface 64 (as illustrated in FIG. 4B). The distal surface 38 is the surface at the distal end of the needle bearing portion 30 from which the needle 40 of the lancet 10 extends axially outwardly from the lancet body 20, and which contacts the skin of a user if the needle 40 fully penetrates the skin of the user (i.e., if the needle 40 penetrates from the distal end or tip 43 to the proximal end 42 of the needle 40).

Preferably, the distal surface 38 of the needle bearing portion 30 extends axially beyond the outer distal surface 64 of the lancing device 60. The area of distal surface 38 should thus be less than the area encompassed by the exit openings 62 of a lancing devices 60 with which it is used, and should be shaped to fit through the exit opening 62. As will be understood by those of skill in the art, the shape and size of the needle bearing portion 30 and distal surface 38 can be altered to correspond to differently sized lancing devices and exit openings 62.

One of the advantages of lancets 10 having a needle bearing portion 30 of the present design for obtaining a blood sample are illustrated in FIG. 5, namely that the depth of skin penetration by the needle 40 is accurately predictable with the use of such a needle bearing portion 30. As long as the present lancet 10 is discharged toward a skin surface 80 with sufficient force so that distal surface 38 of the needle bearing portion 30 contacts the skin surface 80, the needle 40 will predictably penetrate the skin of a user by its entire length (i.e., from its proximal end 42 to distal end 43), as illustrated in FIG. 5C. When using prior art lancets and lancing devices, the needle 40 of the lancet 10 may penetrate deeper or shallower into the skin of a user depending on the condition of the user's skin.

When skin temperature is cold, or the skin is dehydrated, for example, the resistance of the skin to needle penetration increases, and a patient who normally obtains adequate skin penetration using a particular setting of a lancing device may find that performing a lancing procedure at that setting results in inadequate skin penetration (as illustrated in FIG. 5B). The patient is then in the disadvantageous position of needing to perform a further lancing procedure, thereby incurring further pain and needing to use a further lancet 10.

On the other hand, if a user's skin is well-hydrated or warm, the same setting of the user's lancing device 60 may result in skin penetration that is unnecessarily deep, as illustrated in FIG. 5A. Such deep penetration may result in greater pain. Through the use of a pedestal in the lancet 10 of the present lancing system, a consistent depth of puncture can be achieved. This is of particular advantage in systems in which the lancing device 60 does not include a depth adjustment feature, such as a single use disposable lancing device in which the lancet 10 and the system for propelling the lancet 10 are combined in a housing.

The surface area of the distal surface 38 of the needle bearing portion 30 assists in effecting the consistent depth penetration of the present lancets 10, by preventing penetration of the needle 40 into the skin of a user deeper than the length of the needle 40 which extends from the distal surface 38. It is believed that the relatively small surface area of the distal surface 38 also assists in consistent needle penetration by providing a compressive force on the surface of the skin of a user. Penetration of a skin surface by the present lancets is contrasted with skin penetration by prior art lancets in the illustration of FIG. 5D, which illustrates the greater compressive force which can be applied by the relatively smaller surface area of the present lancet (on the viewer's right) as compared to the compressive force applied to a skin surface by the relatively larger surface areas of prior art lancets (if such surfaces were to contact the skin of a user). The surface area of the distal surface 38 is preferably at least 0.5 square mm, and more preferably is between about 0.8 square mm and 3 square mm, though larger surfaces are also possible. The distal surface 38 is preferably generally flat, as a flat surface will provide the greatest compression force to the skin surface of a user.

Pedestal

In one embodiment, the needle bearing portion 30 can taper from a first, larger diameter at a proximal end 33 to a distal end 32 having a second diameter, the second diameter being smaller than the first diameter. The taper is configured so that an outer surface 36 of the needle bearing portion 30 which is proximal to the distal surface 38 of the lancet body (i.e., axially closer to the handle portion 24) contacts an interior surface 66 of the lumen 65 of the lancing device 60 (in order to halt the outward progress of the lancet 10) at a point which places the distal surface 38 of the lancet body 20 at least flush with the outer distal surface 64 of the lancing device 60, and preferably extending axially beyond the outer distal surface 64 of the lancing device 60. This embodiment is illustrated in FIG. 4B and FIG. 6. In a related embodiment, taper can extend from a point on the outer surface 36 of the needle bearing portion 30 to the needle 40 itself, making the surface area of the distal surface 38 small or negligible, for example, having a surface area of less than 1 square millimeter.

Figure 2:
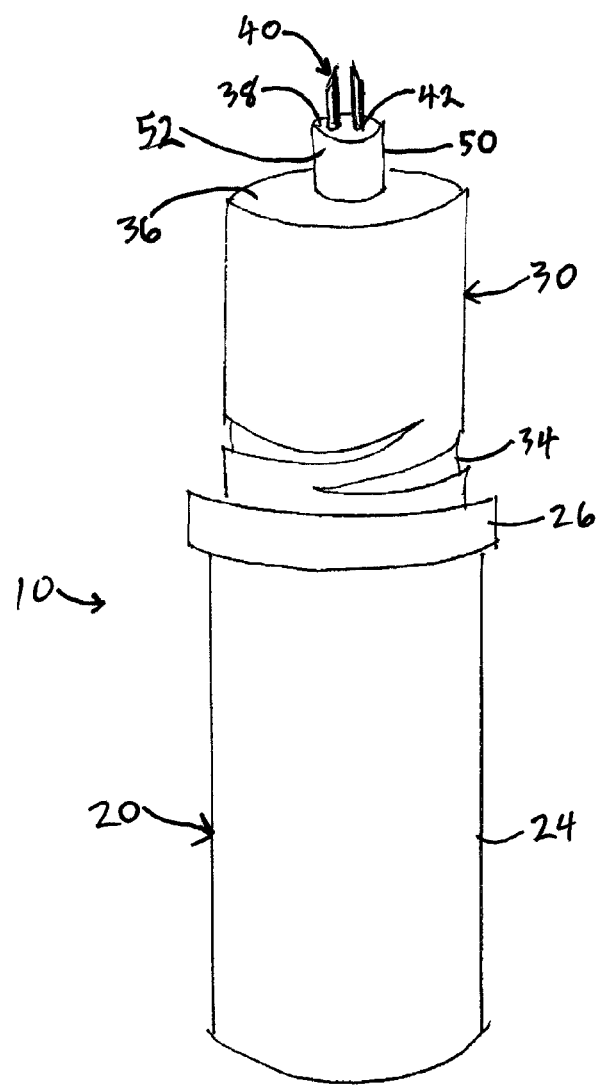
FIG. 2 is a perspective view of an embodiment of the present lancet having two needles.

In an alternative embodiment, shown for example in FIG. 2 and FIG. 7, the needle bearing portion 30 comprises a pedestal 50, i.e. a projecting portion having one or more walls 52 which extend axially outwardly (i.e., further from the handle portion 24) away from the outer surface 36 of the needle bearing portion 30. The pedestal 50 circumscribes the distal surface 38 of the lancet body 20, which is located at a distal end of the pedestal. In this embodiment, the pedestal 50 is shaped and sized to fit through the exit opening 62 of the lancing device 60.

Present lancing devices 60 generally comprise cylindrical exit openings, so a pedestal 50 adapted to be used with such lancing devices 60 is also preferably cylindrical and has a diameter less than that of such exit openings. Most lancing devices 60 have an exit opening of about 3 mm in diameter, so the diameter of the pedestal 50 is preferably between about 1 mm and about 3.5 mm, and more preferably between about 1.5 mm and 2.0 mm, though other diameters are possible (depending on the size of the exit opening 62). The thickness of the wall of lancing devices 60 at such exit openings 62 is generally about 1.0 mm, so if outer surface 36 of the lancet body 20 contacts the interior surface 66 of the lancing device 60 at a point flush with the proximal end of the exit opening 62, the length of the wall 52 should be at least about 1.0 mm, in order to allow it to pass through the exit opening 62.

Needles

The design of the needle bearing portion 30 of the present lancet 10 allows the needles 40 used with the lancet to be both shorter and thinner than the needles used in present lancets. The present needles 40 are preferably between about 0.5 mm and 1.0 mm in length, as measured from the point at which the proximal portion (base) 42 of the needle 40 extends from the distal surface 38 of the needle bearing portion 30. The use of needles of this length allows the present lancet to obtain blood samples with less pain. It is believed that his due at least in part to the anatomy of the outer layers of human skin, i.e. the epidermis and dermis. By using the depth adjustment system of a lancing device 60, a depth of penetration of less than 0.5 mm may produce sufficient bleeding for a blood test in some cases, especially in a child or baby.

The epidermis, i.e. the outer layer of the skin, has no blood vessels and few nerve fibers, and has a depth of about 0.5 mm, though children and babies may have a thinner epidermis, and people with calluses may have a slightly thicker epidermis. The dermis, which lies below the epidermis, has 2 sub-layers, the upper papillary layer and lower reticular layer. The papillary layer has blood vessels and special nerve receptors for touch and pressure, but fewer pain nerve fibers than the reticular layer, which has both blood vessels and pain nerve fibers in abundance. The depth of dermis is generally about 0.5 mm-1 mm, with the papillary layer having a thickness of about 0.125 mm-0.25 mm. Therefore, a puncture by a needle of between 0.3 mm and about 1.0 mm, and more preferably of between 0.5 and 0.75 mm in length will generally be sufficient to cut blood vessels in the papillary layer of the dermis without impacting the pain nerve fibers of the reticular layer.

In view of this, for babies or young children, a shorter needle length is preferably used, such as a length of about 0.5 mm. For children or for adults with thin skin, a 0.75 mm needle length is appropriate, and for adults generally a 1.0 mm needle length can be used. In general, the shortest needle length needed to obtain an appropriate blood sample should be used in the present lancets. The depth of penetration can be further adjusted by using the depth adjustment feature of the lancing device 60. For example, by setting the depth adjustment to a shallower level, the depth of penetration can be even less than 0.5 mm, for example when the present lancet 10 is used with a very young child.

The needles 40 used in the present lancets 10 are also preferably much thinner than those used by current lancets. Commercially available needles of various diameters can be used in the present lancet, but preferably needles of at least 34 gauge (i.e., 34 gauge or smaller), more preferably needles of between 36 gauge and 40 gauge, and more preferably needles of at least 40 gauge, such as 44 gauge needles, are used. Gauge diameters can be rendered in metric units approximately as shown in Table 1 below.

TABLE 1

Needle Diameter Measurements

| Gauge | Diameter in millimeters |
|---|---|
| 34 | 0.234 |
| 35 | 0.213 |
| 36 | 0.193 |
| 37 | 0.173 |
| 38 | 0.152 |
| 39 | 0.132 |
| 40 | 0.122 |
| 41 | 0.112 |
| 42 | 0.102 |
| 43 | 0.0914 |
| 44 | 0.0813 |
| 45 | 0.0711 |
| 46 | 0.0610 |
| 47 | 0.0508 |
| 48 | 0.0406 |
| 49 | 0.0305 |
| 50 | 0.0254 |

Needles having smaller diameters inflict less pain and smaller wounds (less tissue injury) which heal more quickly as compared to larger diameter needles. A puncture by a very thin and short needle causes less tissue injury. The chance of developing excessive callus formation on the fingers, which is often seen in diabetic patients, is also lessened.

The needles 40 can be either solid or hollow and can be formed from various materials. Solid needles are preferred for the present lancing applications, in which fluids are not withdrawn through such needles. The needles 40 can be made of metal, ceramic, plastic, or other appropriate materials. Preferably, a material such as stainless steel is used which can be deformed or otherwise compromised when urged against one of the walls of a chamber of the safety cap 100, as described further below.

A single needle 40 can be used in the present lancet 10, as shown for example in FIG. 6 and FIG. 7. In an alternative embodiment, a plurality of needles 40 can be used with the present lancet 10, as shown for example in FIG. 2 and FIG. 4.

Preferably, each of the needles 40 in this embodiment is arranged in a parallel configuration with respect to each of the other needles 40 retained by the needle bearing portion 30. Although each needle 40 is approximately parallel to each other individual needle, in embodiments in which three or more needles 40 are used in a lancet 10, the needles are preferably arranged in a nonlinear fashion to provide a more compact arrangement of the needles 40 on the needle bearing portion 30 of the body 20. The needles 40 can also project from the lancet 10 by different distances, so that the tips of the needles 40 are adapted to penetrate the skin of a patient sequentially when the lancet 10 is urged toward a skin surface which is approximately perpendicular to the direction of the motion the lancet 10.

Lancet Body

The lancet body 20 of the present lancets 10 preferably comprises a needle bearing portion 30 (described above) and a handle portion 24. The lancet body 20 is preferably formed from an organic polymeric plastic material such as a polyvinyl chloride, polyethylene, or polypropylene. Medical grade plastic materials are known to those of skill in the art.

For ease of manipulation by lancet users, the handle portion 25 can be formed with a relatively thick diameter, as shown for example in FIG. 2 and FIG. 6. In order to provide a surface to engage the rim of a safety cap 100 and help secure the safety cap 100 to the lancet body 20, a circumferential projection or rim 26 can be provided on the distal end of the handle portion 24, as shown in the embodiments illustrated in FIG. 2 and FIG. 6.

In order to reduce the amount of material required to manufacture a lancet, however, lancets having a thinner profile can also be formed, for example for use with ACCU-CHEK® Softclix lancing device (available from Boehringer Mannheim GmbH, Mannheim, Germany). Such "flat" lancets can comprise a tapered needle bearing portion 30, as shown in FIGS. 8A and 8B, or a pedestal 50, as shown in FIGS. 8C and 8D, as well as other features of the present lancets 10.

Safety Caps

In order to prevent needle-stick injuries, in particular with a used lancet which has been exposed to blood, a safety cap 100 is preferably provided for use with the present lancet 10. The present safety cap 100 comprises two chambers, a first chamber 110 having a first opening 112 for enclosing and protecting the needle 40 of the lancet 10 prior to use, and a second chamber 120 having a second opening 122 into which the needle 40 of a used lancet can be placed. In the embodiment of the safety cap 100 illustrated in FIG. 6, the safety cap 100 comprises two opposed ends, with the first opening 112 for the first chamber 110 being located at a first end 102 and the second opening 122 for the second chamber 120 being located at a second end 104. In these illustrated embodiments, the safety cap 100 is approximately cylindrical, with the openings for the first chamber 110 and second chamber 120 positioned on opposed ends of the cylinder and separated by a divider 105, as seen in FIG. 6.

In this embodiment, an outside surface of the safety cap 100 proximal to the second chamber 120 comprises an indicator, such as a color band. If the cap is used correctly, the indicator allows a user to know whether the lancet 10 has already been used, i.e. by indicating to the user that the cap is retained in the second chamber 120. In addition, the safety cap 100 is configured to allow the safety cap 100 to be supported (i.e. stand) on a support surface, such as by being provided with one or more flanges 106. When the safety cap 100 is supported on a support surface by the flange 106, the second opening 122 of the second chamber is preferably oriented upwardly, i.e. directed away from the support surface. In this way, a used lancet 10 can be conveniently inserted into the second chamber 120 without the need for a user to hold the safety cap 100.

The first chamber 110 of the safety cap 100 in this embodiment is designed to cover the needle 40 and at least part of the needle bearing portion 30 of an unused sterile lancet, and acts as a sheath to protect the needle 40, and also preferably assists in maintaining sterility of the needle 40. The first chamber 110 is sized and shaped so as to enclose the needle 40 and at least a portion of the needle bearing portion 30 without structurally compromising the needle 40, as seen for example in FIG. 6E, where the needle 40 and needle bearing portion 30 fit within the first chamber 110. In this embodiment, the first chamber 110 of the safety cap 100 can be securely retained over the needle 40 in any of a variety of ways known to the art. For example, threads 34 on the needle bearing portion 30 of the lancet 10 (shown in FIG. 2) can engage corresponding threads 121 inside the first chamber 110 of the safety cap 100 in order to reversibly secure the lancet 10 to the safety cap 100. Alternatively, the first chamber 110 can be molded around the needle 40 and secured to it by a friction fit, and/or be secured to the needle bearing portion 30 by a co-molded bridging portion designed to be broken off when the safety cap 100 is removed from the needle 40.

The second chamber 120 is also configured to retain at least a distal portion of the needle bearing portion 30, and in some embodiments to retain part of the needle 40. The second chamber 120, however, is configured to bend, deform, break, or otherwise structurally compromise the needle 40 when it is inserted into the second chamber 120 and pressed against an interior surface 124 of the second chamber, thereby rendering it unusable. Preferably, the second chamber 120 is configured to retain the needle bearing portion 30, but has a depth such that when the needle bearing portion 30 is fully inserted into the second chamber 120, the second chamber 120 is not sufficiently deep to fully contain the needle 40. When sufficient force is applied to fully insert the needle bearing portion 30 into the second chamber 120, the needle 40 is placed in contact with a lower surface 125 and is bent or broken, rendering the lancet 10 safe or at least unusable. The lower surface is preferably configured to be at a right angle with respect to the axial orientation of the needle 40 when the lancet body 20 is fully inserted into the second chamber 120 (not including portions of the needle that are bent or damaged), but a lower surface 125 at an acute angle may be preferred in certain embodiments, such as when relatively thicker needles are used. The needle 40 can be physically disabled in such a cap due to the thinness of the needle 40 and by its short length, so that a user can accomplish such disablement by hand (i.e. without the use of a further mechanism).

The short, thin needles, in particular metal needles, used in the present lancets 10 can be disabled in a safety cap 100 made of a plastic material such as polyethylene, while the length and diameter of current lancet needles makes the present solution impractical for such needles (i.e., the larger needles would not be crushed). The selection of a suitably hard plastic material for use as a safety cap 100 for a needle 40 of a particular length and diameter is within the ability of one skilled in the art. In some combinations of the present lancet 10 and safety cap 100, it may be advantageous for manufacturing reasons to use a relatively soft plastic material for molding the safety cap 100, for example to facilitate separation of the safety cap 100 from a co-molded lancet 10. In some cases in which the safety cap 100 is made from such a relatively soft plastic, the needle 40 may tend to pierce the lower surface 125 rather than be bent or broken. In such cases it is advantageous to provide the second chamber 120 with a sloping interior surface 124, as shown in FIG. 6 and FIG. 7A. The interior surface 124 in this embodiment is sloped at an angle which is acute with respect to the axial orientation of the needle 40 when the lancet body 20 is fully inserted into the second chamber 120. When the needle 40 is placed in contact with such a sloping surface at an acute angle, i.e. an angle of less than 90°, and force is applied by a user, for example in a downwardly direction toward lower surface 125, this will act to bend the needle 40 and possibly break it, and/or to weaken the needle 40 so that it can be further bent or broken when placed into contact with the lower surface 125.

Figure 3:
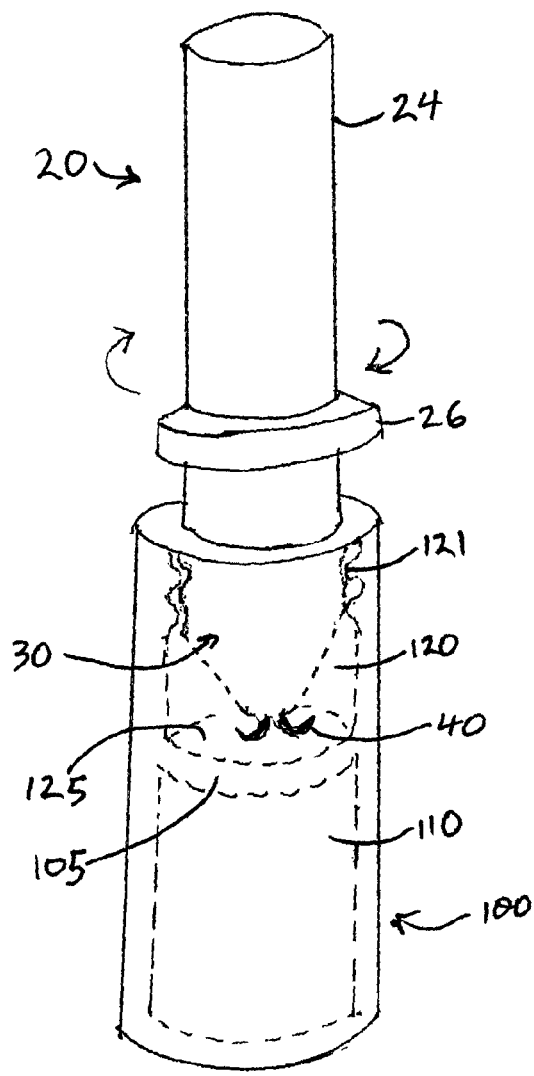
FIG. 3 is a perspective view of an embodiment of the present lancet having two needles after being inserted into an embodiment of the present safety cap.

The second chamber 120 of the safety cap 100 is preferably provided with a mechanism for securing the needle bearing portion 30 of the lancet in the second chamber 120, in order to hold the cap in place when the safety cap 100 is covering a used lancet. Such securing can be in a reversible manner, such as through the use of screw threads 34 on the needle bearing portion 30 which engage corresponding threads 121 on the interior surface of the second chamber 120, as shown in FIG. 3. In a preferred embodiment, however, the second chamber 120 of the safety cap 100 is fixedly secured to the needle bearing portion 30 of the lancet 10, i.e. it is secured in a manner which is not designed to be reversible or in a manner such that the safety cap 100 cannot be removed from the lancet 10 once the lancet 10 is secured within the second chamber 120 without breaking or otherwise compromising the structure of either the safety cap 100 or the lancet 10.

One mechanism for fixedly securing the present lancet 10 within the second chamber 120 of the safety cap is shown in FIGS. 7 and 9. In this embodiment, a structure adjacent the rim 127 of the second chamber 120 is configured to engage a corresponding structure on the lancet body 20 of the lancet 10, and preferably to engage a structure on the needle bearing portion 30, in order to securely retain the safety cap 100 on the lancet 10 in a fixed manner. In the embodiments illustrated in FIG. 7 and FIG. 9, a plurality of flanges 123 projecting inwardly from the rim 127 are provided in order to securely retain the lancet 10. One or more receptacles 35 are formed in the lancet body 20, preferably in the needle bearing portion 30, for retaining the flanges 123 once the lancet 10 is inserted into the second chamber 120. In the embodiments of FIGS. 7 and 9, the receptacle 35 is an annular groove, and a shoulder 39 is provided on the needle bearing portion 30 distally of the receptacle 35. When the lancet body 20 is inserted into the second chamber 120 in this embodiment, the shoulder 39 is pushed past the flanges 123 in order for the flanges 123 to engage the receptacle (groove) 35. The use of a plastic material with some flexibility and/or the use of a rounded surface on the shoulder 39 can facilitate placement of the shoulder 39 into the second chamber 120 and past the flanges 129. The flanges 123 then hinder and/or prevent the removal of the lancet from the safety cap 100.

The flanges 123 can, in one embodiment, be semi-spherical in shape, and are preferably smooth (not angular) so as to facilitate getting the shoulder 39 past the flanges 123 when placing the needle bearing portion 30 into the second chamber 120. However, the portion of the flange 123 facing the interior of the chamber (i.e., toward lower surface 125) preferably include an angled surface, such as a surface at an acute or right angle to the inner wall of the second chamber 120, so as to make it difficult to remove the lancet 10 once it is inserted into the second chamber 120 of the safety cap 100. Alternatively, such flanges 123 can project both inwardly and downward (i.e. toward the lower surface 125), thus forming a hook shaped circular rim. In another alternative embodiment, the lancet body 20 can be provided with one or more flanges, similar to the flanges 123, and the safety cap 100 can instead be provided with one or more receptacles for receiving such flanges on the lancet body 20. In this embodiment, the flanges on the lancet body 20 can be molded with and integrally attached to the lancet body 20. If the safety cap 100 is molded together with the lancet 10, and if the first chamber 110 is sized so as to fit around the flanges provided on the lancet body 20, the flanges can be connected to the safety cap 100, and can be designed to separate from the safety cap 100 when the safety cap 100 is removed from the lancet 10, such as through the application of a twisting motion to the safety cap 100 by a user. By fixedly securing the lancet body 20, and in particular needle bearing portion 30, within the second chamber 120, the need for safely disposing of the needle 40 in, for example, a sharps container is obviated.

In the embodiment of the lancet 10 and safety cap 100 combination shown in FIG. 6, the needle bearing portion 30 comprises a conically shaped portion that tapers from a larger outer diameter at a proximal end 33 to a smaller diameter at a distal end 31 adjacent the needle 40. A circular, wedge-shaped groove 35 is formed in the needle bearing portion 30 proximal to the conically shaped portion, such that the conical portion comprises a lower surface 37. The second chamber 120 of the safety cap 100 is formed with a reciprocal space for retaining the conically shaped portion, and further includes a circumferential protrusion 126 that serves to lock in the conically shaped needle bearing portion 30 once it is inserted into the second chamber 120. In this embodiment, the lancet body 20, or at least the needle bearing portion 30, are formed from a plastic which is sufficiently deformable that when pressed into the second chamber 120, the proximal end 33 of the conically shaped portion can be compressed sufficiently to pass the circumferential protrusion 126 and enter the reciprocally-sized and shaped space of the second chamber 120. A proximal surface of the circumferential protrusion 126 will then serve to retain the needle bearing portion 30 in the second chamber by contacting the lower surface 37 of the conical needle bearing portion 30. Once the conical portion is inserted into the safety cap 100, it can not be removed without risking compromising the structure of the safety cap 100 or lancet 10.

Figure 6A:
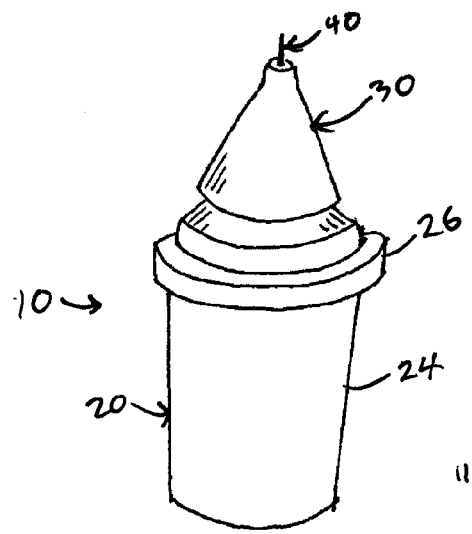
FIG. 6A is a perspective view of another lancet of the present invention.
Figure 6C:
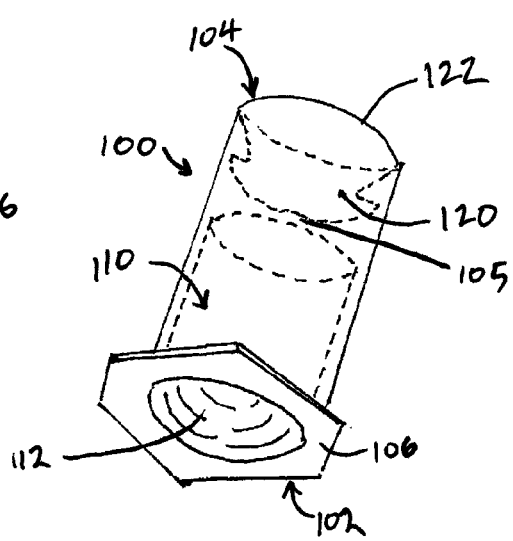
FIG. 6C is a perspective view of a safety cap for use with the lancet of FIG. 6A.
Figure 6B:
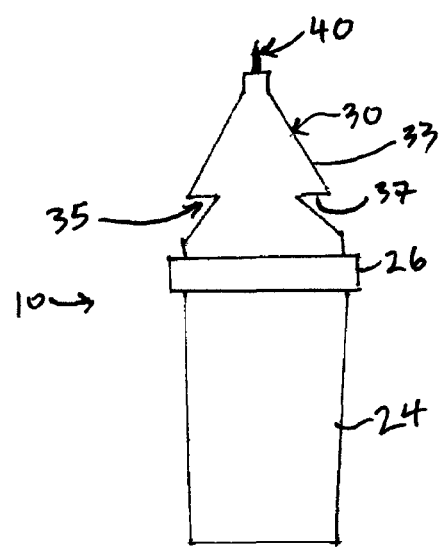
FIG. 6B is a side plan view of the lancet of FIG. 6A.
Figure 6D:
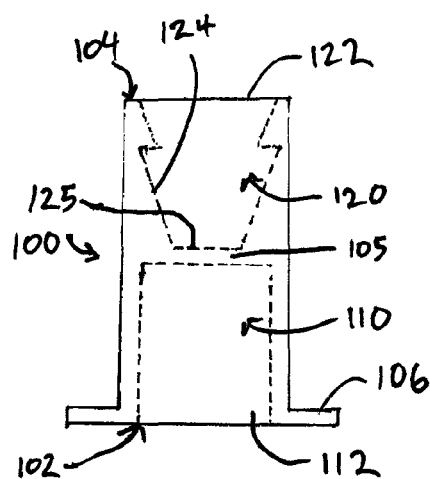
FIG. 6D is a side sectional view of the safety cap of FIG. 6C.

FIG. 6E through FIG. 6H illustrate the use of this embodiment of the safety cap 100 and lancet 10. FIG. 6E shows an unused lancet 10 where the first chamber 110 covers the unused, sterile needle 40. FIG. 6F shows the lancet 10 removed from the first chamber 110 of the safety cap 100, prior to use. Following use, the safety cap 100 can be placed on a flat support surface such that the lower surface of the flange 106 supports the safety cap 100 on the support surface, as shown in FIG. 6G, in which a used lancet 10 is positioned over the opening 122 of the second chamber 120. When the needle bearing portion 30 is placed completely into the second chamber 120, as shown in FIG. 6H, the needle 40 is placed into contact with the lower surface 125, thereby breaking the needle 40. It will be understood by one skilled in the art that the second chamber 120 can have one or more additional interior surfaces 124 for compromising the structure of the needle 40 when the needle bearing portion 30 is inserted.

FIG. 7 illustrates a further embodiment of a lancet 10 and safety cap 100 combination, in which both the lancet body 20 and the safety cap 100 can be manufactured in a single injection molding process, thus saving manufacturing cost and time. In this embodiment, the safety cap 100 is molded around the distal portion of the needle 40, and the first chamber 110 thus covers and retains only the needle 40 of the lancet 10 (best seen in FIG. 9C, which illustrates a similar embodiment) and not the needle bearing portion 30. Due to the thin diameter of the needles 40 used in the present lancets 10, safety caps 100 formed in this way are preferably smaller than those illustrated in FIGS. 3 and 6, as larger and heavier caps attached directly to the needle 40 may tend to bend the needle 40. In the illustrated embodiment, the safety cap 100 is approximately cylindrical in shape, although other shapes are also possible.

In one embodiment, one or more flanges 130 are provided to stabilize the safety cap 100 while it is retained on the lancet 10, in particular when the first chamber 110 of the safety cap 100 retains only the needle 40. As shown in FIG. 9, the flange 130 extends downwardly from the safety cap 100, i.e. toward the needle bearing portion 30 of the lancet body 20, and is preferably parallel to the needle 40 and/or to the walls 52 of the pedestal 50 (if present). Although one flange 130 is shown in FIG. 9, a plurality of flanges 130 can also be used to stabilize the safety cap 100 while it is retained on the lancet 10.

In one embodiment involving the use of flanges 130, the flange 130 extends to and contacts the needle bearing portion 30 and partially supports the weight of the safety cap 100. The flange 130 can in this case be integrally molded together with the needle bearing portion 30. In order to remove the safety cap 100 from the needle 40 in this embodiment, the safety cap 100 is preferably twisted, thereby breaking the connection between the flange 130 and the needle bearing portion 30, and/or between the flange 130 and the safety cap 100.

Figures 9A, 9B, 9C:
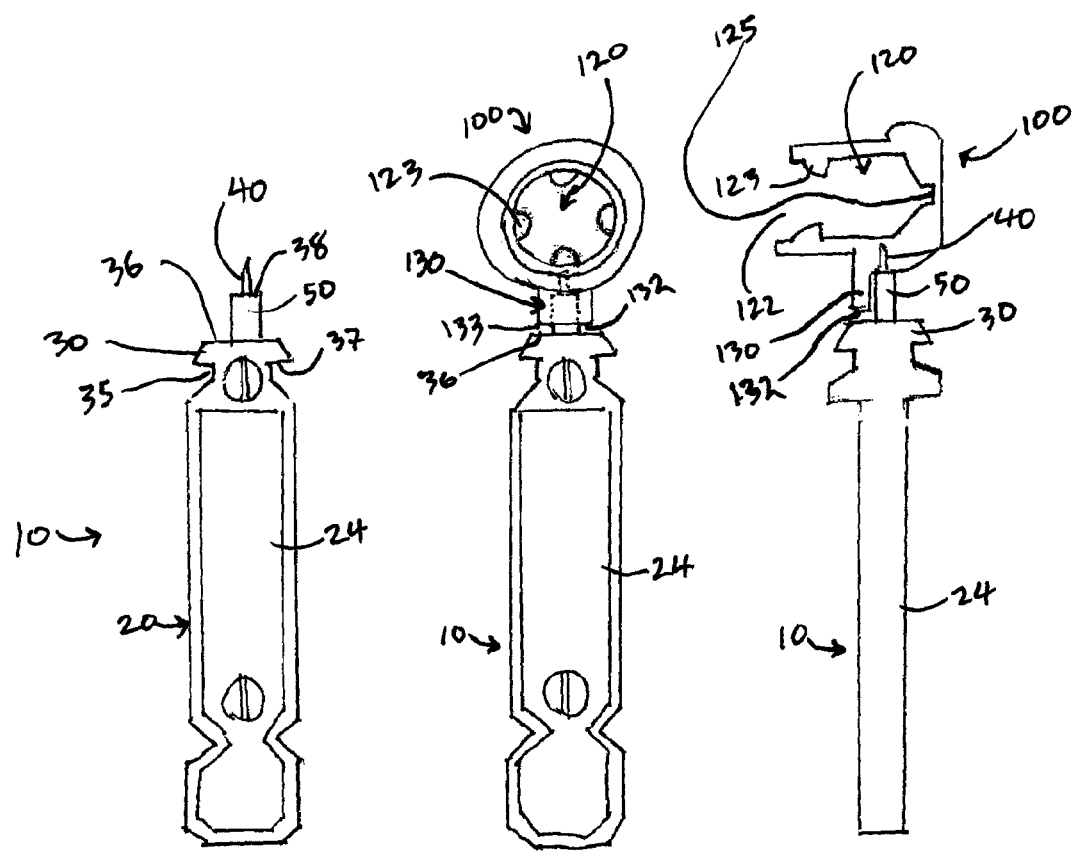
FIG. 9A is a plan view of yet another embodiment of the present lancet.
FIG. 9B is a plan view of the safety cap of FIG. 7A retained on the lancet of FIG. 9B.
FIG. 9C is a side view of FIG. 9C.

In a preferred embodiment, shown in FIG. 9, the flange 130 is molded with the safety cap 100, and while the safety cap 100 is retained on the needle 40 the flange 130 extends toward the needle bearing portion 30 but doesn't contact needle bearing portion 30, i.e. its distal end terminates adjacent to the surface of the needle bearing portion 30. In this embodiment, the flange 130 preferably comprises a lower surface 132 approximately parallel to the outer surface 36 of the needle bearing portion 30 to which it is adjacent. The inclusion of such a lower surface 132 helps to protect the needle 40 from becoming bent by inadvertent movement of the safety cap 100. As can be seen in FIG. 9B, if the cap is urged in a lateral direction, i.e. along the length of the lower surface 132, a lateral end of the lower surface 132 will be placed into contact with the outer surface 36 of the needle bearing portion 30. For example, if the safety cap 100 illustrated in FIG. 9B is urged to the viewer's left, then lateral end 133 of the flange 130 will contact the outer surface 36 and resist the further movement of the safety cap 100 in that direction.

The safety cap 100 shown in FIGS. 7 and 9 comprises a cylindrical compartment in the bottom center of the second chamber 120 which is configured to tightly accommodated the needle bearing portion 30 of the lancet 10, and in the illustrated embodiment is shaped and sized to accommodate a pedestal 50. In addition, the interior wall of the second chamber 120 slopes from cylindrical chamber toward the rim 127 of the second chamber 120, thus facilitating the placement of the needle bearing portion 30 of a used lancet 10 into the cylindrical compartment.

Lancing Devices

Figure 10:
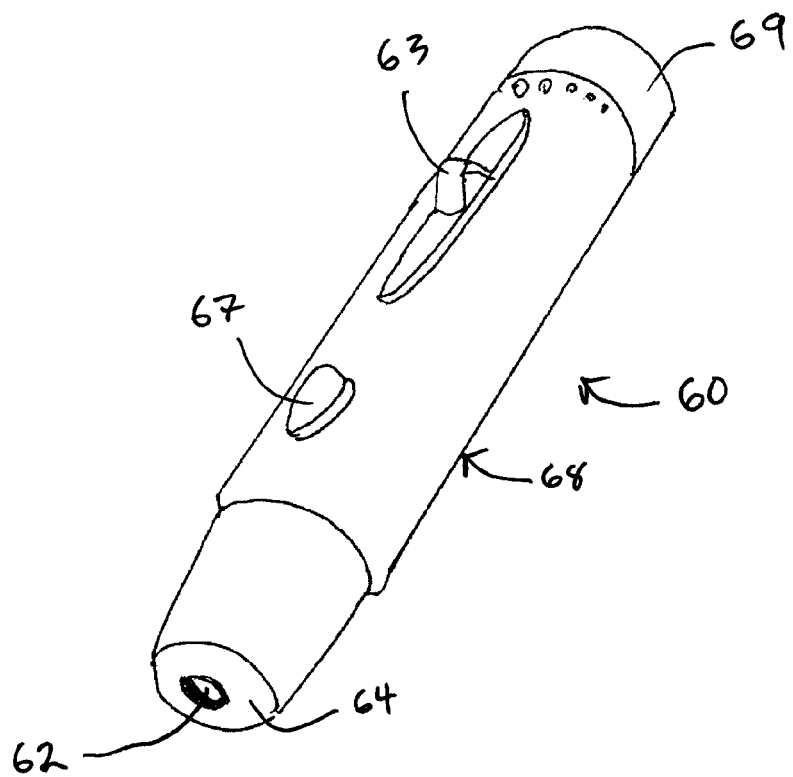
FIG. 10 shows a prior art lancing device.

A variety of commercial lancing devices can be used with the lancet 10 and safety cap 100 of the present invention, such as the SOFTCLIX II device (available from Boehringer Mannheim GmbH, Mannheim, Germany), the BD Lancet Device (available from Becton, Dickinson and Company, Franklin Lakes, N.J., USA), or the PENLET PLUS device (available from LifeScan, Milpitas, Calif., USA). In one embodiment, as shown in FIG. 10, the lancing device 60 can comprise an elongate cylindrical housing 68 having essentially the shape of a pen. Lancing devices 60 include in their interior an ejector, i.e. a mechanism which guides a lancet 10 in the lancing process through an interior portion (lumen) 65 (see FIG. 4) towards and, after lancing, away from the desired lancing site on the skin of a user of the device 60. During the lancing process, the needle(s) 40 of the lancet 10 pass through an exit opening 62 of the lancing device 60. This mechanism can be driven, e.g., by a manually tensioned spring. A cocking lever 63 can be present on the housing 58 to set the mechanism, and a triggering button 67 can be present on the housing 68 of the lancing device 60 to trigger the mechanism. The lancing devices 60 can be reusable can reversibly retain one or more lancets 10, which can be removed after use and replaced with unused, clean lancets 10.

Such pen-shaped lancing devices preferably include a depth adjustment control knob 69. When a deeper puncture is desired, for example to produce a greater amount of blood or to penetrated callused skin, the knob 69 can be adjusted to make the needle penetrate the skin deeper. In one embodiment, the length of one or more needles mounted on a lancet can be different from one or more other needles. By adjusting the depth adjustment control knob 63 of the lancing device 60, patients can in this way have a choice of one needle puncture or 2 or more simultaneous punctures.

In a further embodiment, the lancing device 60 can be a single use device in which the present lancet 10 is pre-loaded into the device prior to being provided to a user. Such devices typically comprise a plastic housing which encloses a spring mechanism for propelling a lancet 10 through the exit opening 62 upon the actuation of a triggering button 67. The needle 40 is typically retracted into the housing of the lancing device 60 of this embodiment following use.

Methods of Use

The present lancet 10 can be used to puncture the skin of a patient either manually by hand, or mechanically by a lancing device 60. In both cases a user of the lancet 10 first cleans the skin of the area of skin which is to be punctured by the needle or needles 40, such as with an alcohol swab, in order to prevent infection at the lancing site. When used manually, the handle portion 24 of the lancet body 20 is held with the fingers, and the needle 40 of the lancet 10 is directed to the cleansed skin area and jabbed into the skin. The needle 40 is immediately withdrawn from the skin.

When used in conjunction with a lancing device 60, the present lancet 10, which preferably includes a safety cap 100, is first inserted into a lancet holder of the lancing device 60, and the safety cap 100 is removed, thereby exposing the needle 40. The lancing device 60 is then closed to secure the lancet 10 for a lancing procedure. The outer distal surface 64 of the lancing device 60 is then placed on the skin surface to be lanced. If necessary, the lancing device 60 is cocked, i.e. the tensioning spring is put under tension, such as with a cocking lever 63 (see FIG. 10). The lancing device 60 is then actuated, such as by depressing a triggering button 67, to cause the lancet 10 to be propelled to the skin of a user and puncture it. The distal surface 38 of the needle bearing portion 30 pass into and preferably completely through the exit opening 62 of the lancing device 60 and preferably contacts skin of the user after the needle 40 has punctured it.

After lancing, a small droplet of blood may appear spontaneously at the lancing site, usually 2-20 μl in volume. Otherwise, blood samples can then be obtained by gently squeezing the pricked skin. The area of the skin punctured by a lancet can be the finger, palm, heel, foot, earlobe, or any part of the body where a desired blood sample can be obtained. Once an adequate amount of blood for a particular test has been obtained, the sample can be subjected to testing, such as on a test strip for use with a glucose meter. Other analytical tests for determining other constituents or properties of a blood sample can also be performed with a blood sample obtained with the present lancets.

Following the use of one of the present lancets 10 in a lancing procedure, the needle 40 and at least a part of the needle bearing portion 30 lancet is preferably inserted into the second chamber 120 of the safety cap 100 in order to structurally compromise the needle 40. When a lancing device 60 is used, the lancet 10 can be inserted into the second chamber 120 before the used lancet 10 is removed from the lancet holder of the lancing device 60, and once the needle 40 is impacted in the second chamber 120 of the safety cap 120, the whole used lancet 10 with the safety cap 100 on it can be taken out of the lancing device 60, in order to avoid needle-stick injuries. Alternatively, the lancet can be removed from the device and then placed into the second chamber 120 of the safety cap 100. The used lancet 10 safely capped with the safety cap 10 can then be discarded.

EXAMPLES

Example 1

Patients in need of blood glucose level monitoring used lancets as described herein to obtain blood samples. The lancets had a needle 1 mm long and 0.15 mm in diameter which was mounted on a 2 mm long and 1.75 mm in diameter pedestal. Patients also made use of conventional lancets having a 3 mm long, 0.3 mm thick needle.

Lancing procedures with both lancets were performed using the "One-Touch" lancing device produced by Lifescan or the "Freestyle" lancing device produced by Abbott Laboratories. Blood was obtained from finger tip skin of the patients.

All patients reported experiencing less puncture pain when using the present lancets than when using the conventional lancets. All patients punctured by the present lancets produced enough blood volume for glucose testing.

Example 2

Thirty diabetic patients were enrolled in an open, randomized clinical study to test the present lancet. The needle of the lancet was 0.75 mm in length and 0.15 mm in diameter. The pedestal was 2.25 mm in length, and the diameter of the top surface of the pedestal was 1.75 mm.

The patients were asked to rate the pain experienced when using the lancet, using a pain scale ranging from 0-3, as detailed in Table 2 below.

| Pain Number | Self-reported Pain Level |
| --- | --- |
| 0 | no pain |
| 1 | slight pain |
| 2 | moderate pain |
| 3 | severe pain |

All patients using the present lancet reported a pain number of "0" in connection with the use of this lancet. The pain number reported for other lancets ranged from 0-3, with the average being 1.5 and the median being 1. All patients claimed that the new lancet was pain free.

CONCLUSION

The present invention has several advantages. The shorter and thinner needles of the present invention are less painful when puncturing the skin. In addition, wound healing is faster with a smaller puncture wound by a thinner needle than that of a larger needle. An additional advantage of the present invention is that the short and thin needles look less intimidating, which is very helpful for children with diabetes who are often frightened by a long and thick needle. The use of less intimidating needles is also likely to increase compliance by diabetic patients, and better monitoring of blood glucose levels by such patients can reduce the incidence of the complications of diabetes, including blindness, kidney failure and amputation of the limbs.

Another advantage is that the thin and short needles of the present invention are easily breakable. Once the sharp needle is flattened, bent, broken or crushed, the chance of injury is much less. Another advantage is that the covering cap of the lancet needle has two compartments to prevent an accidental needle injury by used lancet needles. Once threaded into the used compartment of the covering cap, the lancet is destroyed and safely locked to prevent accidental injury. Even if the cap is unscrewed from the lancet, the bent, flattened, or broken needles cannot be used again by accident.

Although the present invention has been discussed in considerable detail with reference to certain preferred embodiments, other embodiments are possible. The steps disclosed for the present methods are not intended to be limiting nor are they intended to indicate that each step is necessarily essential to the method, but instead are exemplary steps only. Therefore, the scope of the appended claims should not be limited to the description of preferred embodiments contained in this disclosure.

All references cited herein are hereby incorporated by reference herein in their entirety. All dimensions specified in this disclosure are by way of example only and are not intended to be limiting. Further, the proportions shown in these Figures are not necessarily to scale. As will be understood by those with skill in the art with reference to this disclosure, the actual dimensions of any device or part of a device disclosed in this disclosure will be determined by its intended use.

What is claimed is:

1. A lancing system, comprising:
   (a) a lancing device capable of retaining a lancet and, when actuated, urging the lancet forward to puncture a skin surface of a user, the lancing device having an exit opening; and
   (b) the lancet for use with the lancing device, the lancet comprising:
      (i) a needle bearing portion having a proximal end and a distal end, the proximal end comprising a proximal surface having a first diameter, the distal end comprising a distal surface having a second diameter, the second diameter being smaller than the first diameter, wherein the distal end of the needle bearing portion comprises a pedestal, the pedestal comprising one or more walls extending axially outwardly from the proximal surface of the needle bearing portion to the distal surface of the needle bearing portion, wherein the one or more walls of the pedestal circumscribe the distal surface of the needle bearing portion and have a length of at least 1.0 millimeter, and wherein the distal surface of the needle bearing portion extends through an exit opening of a lancing device and contacts the skin surface of the skin of the user when the longitudinal extent of the needle is fully embedded in the skin surface of the user, thereby producing a predictable depth of penetration of the user's skin;
      (ii) a handle portion attached to the proximal end of the needle bearing portion; and
      (iii) a needle having an exterior portion extending from the distal surface of the needle bearing portion, the exterior portion of the needle having a needle proximal end, a needle distal end, and a longitudinal extent between the needle proximal end and the needle distal end, wherein the needle proximal end is in contact with the distal surface of the needle bearing portion.

2. The lancing system of claim 1, wherein protrusion of the needle and the distal surface of the needle bearing portion from the exit opening is limited by contact between an outer surface of the needle bearing portion and an interior surface of the lancing device.

3. The lancing system of claim 1, wherein the distal surface of the needle bearing portion has an area of up to 12 square millimeters.

4. The lancing system of claim 1, wherein the distal surface of the needle bearing portion has a surface area of at least about 0.5 square millimeter.

5. The lancing system of claim 1, wherein the distal surface of the needle bearing portion has a surface area of between about 0.8 square mm and 3 square mm.

6. The lancing system of claim 1, wherein said distal surface of the needle bearing portion is substantially flat.

7. The lancing system of claim 1, wherein the pedestal is cylindrical and has a diameter of between about 1 millimeter and about 3.5 millimeters.

8. The lancing system of claim 1, wherein the longitudinal extent of the needle is between about 0.3 millimeters and about 1.0 millimeters.

9. The lancing system of claim 1, wherein the longitudinal extent of the needle is between 0.5 and 0.75 millimeters.

10. The lancing system of claim 1, wherein the needle is a 36 gauge needle.

11. The lancing system of claim 1, wherein the longitudinal extent of the exterior portion of the needle is less than about 1.0 millimeter.

12. The lancing system of claim 1, wherein the needle has a diameter of less than about 0.2 millimeter.

13. The lancing system of claim 1, wherein the lancing device further comprises a depth adjustment mechanism.

14. A method for puncturing skin of a subject with a lancet, said skin comprising an epidermis and a dermis having a papillary layer and a reticular layer, comprising:
   (a) providing a lancing system comprising:
      (i) a lancet comprising:
         a needle bearing portion having a proximal end and a distal end, the proximal end comprising a proximal surface having a first diameter, the distal end comprising a distal surface having a second diameter, the second diameter being smaller than the first diameter, wherein the distal end of the needle bearing portion comprises a pedestal, the pedestal comprising one or more walls extending axially outwardly from the proximal surface of the needle bearing portion to the distal surface of the needle bearing portion, wherein the one or more walls of the pedestal circumscribe the distal surface of the needle bearing portion and have a length of at least 1.0 millimeter, and wherein the distal surface of the needle bearing portion extends through an exit opening of a lancing device and contacts the skin surface of the skin of the user when the longitudinal extent of the needle is fully embedded in the skin surface of the user, thereby producing a predictable depth of penetration of the user's skin;

a handle portion attached to the proximal end of the needle bearing portion; and a needle having an exterior portion extending from the distal surface of the needle bearing portion, the exterior portion of the needle having a needle proximal end, a needle distal end, and a longitudinal extent between the needle proximal end and the needle distal end, wherein the needle proximal end is in contact with the distal surface of the needle bearing portion; and (ii) a lancing device capable of retaining the lancet and, when actuated, urging it forward to puncture a skin surface of a user, the lancing device having an exit opening;

(b) puncturing the subject's skin with the lancet such that the distal surface of the needle bearing portion of the lancet presses against the skin and the needle is fully embedded in the skin; and (c) withdrawing the needle from the skin, thereby consistently and painlessly cutting blood vessels in the papillary layer and producing a predictable depth of penetration.

15. The method of claim 14, wherein the longitudinal extent of the exterior portion of the needle of the lancet is less than about 1.0 millimeter.

16. The method of claim 14, wherein the needle of the lancet has a diameter of less than about 0.2 millimeter.

\* \* \* \* \*